(12) United States Patent
Clark

(10) Patent No.: US 6,522,471 B2
(45) Date of Patent: Feb. 18, 2003

(54) SYSTEM OF BEAM NARROWING FOR RESOLUTION ENHANCEMENT AND METHOD THEREFOR

(75) Inventor: Bryan Kevin Clark, Mountain View, CA (US)

(73) Assignee: Z Tek Inc., Fremont, CA (US)

( * ) Notice: Subject to any disclaimer, the term of this patent is extended or adjusted under 35 U.S.C. 154(b) by 40 days.

(21) Appl. No.: 09/789,913

(22) Filed: Feb. 21, 2001

(65) Prior Publication Data

US 2002/0113974 A1 Aug. 22, 2002

(51) Int. Cl.[7] .......................... G02B 27/14; H01L 29/06; H01S 3/10
(52) U.S. Cl. .......................... 359/629; 359/318; 257/21; 372/26; 250/214.1; 356/450
(58) Field of Search ................................. 359/629, 318, 359/559, 565; 257/21, 437; 372/20, 22, 26, 45, 50; 250/214.1; 356/450, 507

(56) References Cited

U.S. PATENT DOCUMENTS

| | | | |
|---|---|---|---|
| 5,222,071 A | * | 6/1993 | Pezeshki et al. .............. 372/26 |
| 5,486,924 A | | 1/1996 | Lacey .......................... 356/507 |
| 5,818,592 A | | 10/1998 | Womack et al. ............ 356/450 |
| 6,380,531 B1 | * | 4/2002 | Sugihwo et al. ......... 250/214.1 |

* cited by examiner

Primary Examiner—Loha Ben
(74) Attorney, Agent, or Firm—Jeffrey D. Moy; Mitch Harris; Weiss, Moy & Harris, P.C.

(57) ABSTRACT

A system of beam narrowing for resolution enhancement produces a narrowed beam for use in surface imaging. The system of beam narrowing for resolution enhancement uses a Fabry-Perot cavity to sharpen the intensity profile of a light source imaged through the system. The optical distance between reflective surfaces forming the Fabry-Perot cavity is tuned to select one of the surfaces as a target surface. The beam width is thereby optimized to a minimum width at the selected target surface. Multiple Fabry-Perot cavities can be cascaded by interposing one or more additional partly reflective surfaces between a first surface and a second underlying surface. The optical distances between all of the surfaces are tuned to select a target surface. The beam width is optimized at the selected target surface to produce a beam narrower than the beam produced by a single Fabry-Perot cavity.

25 Claims, 4 Drawing Sheets

SYSTEM OF BEAM NARROWING FOR RESOLUTION ENHANCEMENT AND METHOD THEREFOR

BACKGROUND OF THE INVENTION

1. Field of the Invention

This invention relates to resolution enhancement, and more specifically, to a system of beam narrowing for resolution enhancement utilizing a Fabry-Perot cavity and a method therefor.

2. Description of the Related Art

The ability to resolve surfaces of interest and any details thereon is generally limited by the diffraction limits of the optics utilized. The physical specifications of the optical system and the illumination system determine the value of this lower limit of resolution. The effects of the diffraction limits are a result of the propagation of the electromagnetic field.

Some of the known methods related to the minimization of the diffraction limitations, or compensating for them, include immersion microscopy, near-field imaging, confocal imaging, phase modulation of microlithographic masks, etc. These known methods all have drawbacks however. The drawbacks may result from the need for special system configurations, or due to the specifics of each of the known methods, their practicality is limited to special case applications, and the known methods are also quite expensive and task dedicated. Thus—the problem still to be solved is resolution enhancement in a system and method that is easily and inexpensively implemented for a large number of applications. A problem requiring a solution that addresses the resolution/diffraction limitations is a system of beam narrowing for resolution enhancement utilizing a Fabry-Perot cavity.

Therefore, a need existed for a system for resolution enhancement and a method therefor. Another need existed for a system for resolution enhancement that is inexpensive to implement and a method therefor.

SUMMARY OF THE INVENTION

It is an object of the present invention to provide a system for resolution enhancement and a method therefor. It is another object of the present invention to provide for a system for resolution enhancement that is inexpensive to implement and a method therefor.

The foregoing and other objects, features, and advantages of the invention will be apparent from the following, more particular, description of the preferred embodiment of the invention, as illustrated in the accompanying drawings.

BRIEF DESCRIPTION OF THE PREFERRED EMBODIMENTS

According to one aspect of the invention, a first embodiment of a system of beam narrowing for resolution enhancement is disclosed. The system of beam narrowing for resolution enhancement includes an illumination system, a surface of interest positioned in a plane relative to the illumination system, and an optical focusing system positioned in a plane relative to the illumination system. The optical focusing system cooperates with the illumination system to image a light source through the illumination system and through the optical focusing system onto a selected target surface. A reference plate is included and is positioned between the optical focusing system and the surface of interest. The reference plate has an inner partly reflective surface substantially parallel to the surface of interest, and the reflective surface is further positioned at a tuned optical distance from the surface of interest and the tuned optical distance is defined as that value where the image spot size of the light source on the selected target surface is minimized.

According to another aspect of the invention, a second embodiment of a system of beam narrowing for resolution enhancement is disclosed. The second embodiment of the system of beam narrowing for resolution enhancement includes an illumination system, a surface of interest positioned in a plane relative to the illumination system and an optical focusing system positioned in a plane relative to the illumination system. The optical focusing system cooperates with the illumination system to image a light source through the illumination system and through the optical focusing system onto a selected target surface. A reference plate is included and is positioned between the optical focusing system and the surface of interest. The reference plate has an inner partly reflective surface substantially parallel to the surface of interest. Several other partly reflective surfaces are included and are positioned between the first partly reflective surface and the surface of interest and are positioned substantially parallel to the first partially reflective surface. The relative distances between any and all of the partly reflective surfaces and the selected target surface are tuned so that the image spot size of the light source on the selected target surface is at a minimum.

DESCRIPTION OF THE PREFERRED EMBODIMENTS

Figure 1:
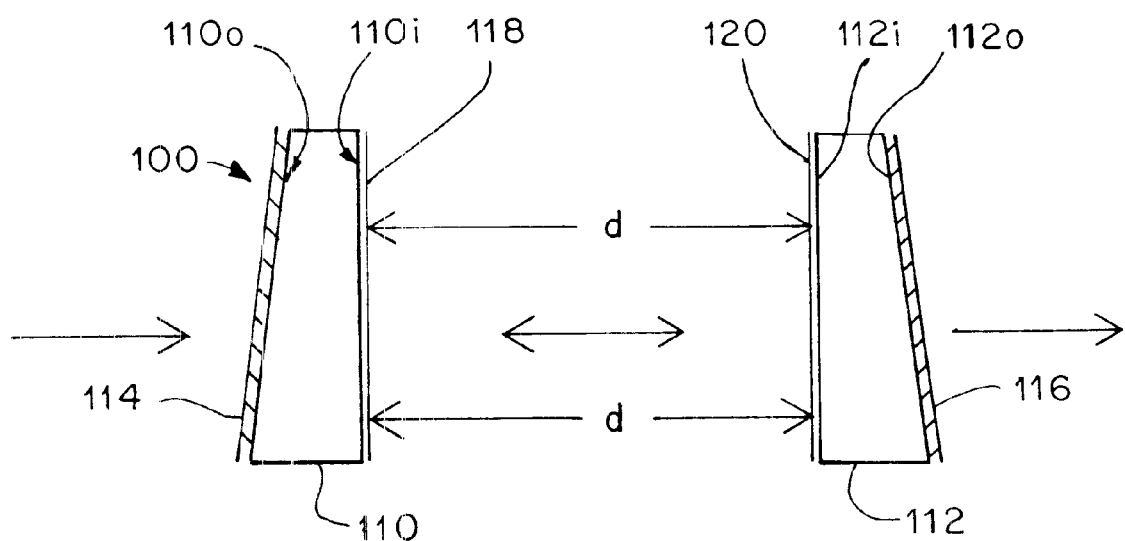
FIG. 1 is a simplified schematic of a Fabry-Perot device whereby the present invention may be practiced.

Referring to FIG. 1, a simplified schematic of a Fabry-Perot device that depicts a fundamental physics principle of an embodiment of the present invention is shown. A Fabry-Perot device is an optical resonator where the distance between the plates equals the length of specific frequencies in the optical wavelength spectrum. A Fabry-Perot device has various uses in laser technology, spectrometry, thin or thick films, etc. due to its optical resonant properties. Embodiments of the present invention possess key phenomena resulting from the formation and usage of a Fabry-Perot cavity in a specifically tuned manner. One of these phenomena is enhanced lateral resolution, or beam narrowing.

Referring again to FIG. 1, the simplified schematic of a Fabry-Perot device 100 is shown. The principles of operation of a Fabry-Perot device are discussed in detail in *OPTICS* by Eugene Hecht & Alfred Zajac, published by the Addison-Wesley Publishing Company ©1974. A Fabry-Perot device 100 is comprised of two planar partly reflective plates 110 and 112. The partly reflective plates 110 and 112 possess partly reflective properties, since inner surfaces 110*i* and 112*i* are partly reflective. The partly reflective plates 110 and 112 may be coated with coatings 118 and 120 that are either dielectric coatings or metallic coatings, in either single or multiple layers, in order to provide partly reflective surface properties. Inner surfaces 110*i* and 112*i* are parallel to one another, and are separated by a distance d.

More sophisticated configurations of Fabry-Perot devices 100 may be constructed. For example, the partly reflective plates 110 and 112 may be constructed from non-rectilinear shapes, and may be oriented in non-parallel configurations. Also, as shown in FIG. 1, the outer surfaces 110*o* and 112*o* of partly reflective plates 110 and 112 are not necessarily parallel to the inner surfaces 110*i* and 112*i* although they may be. (Note that non-parallel construction is exemplified in FIG. 1.)

In addition to the foregoing, wherein two inner surfaces 110*i* and 112*i* form a Fabry-Perot cavity, one surface may be a partial mirror plate with its inner surface being partly reflective and the other plate may be either a full mirror or a surface of interest.

Figure 2:
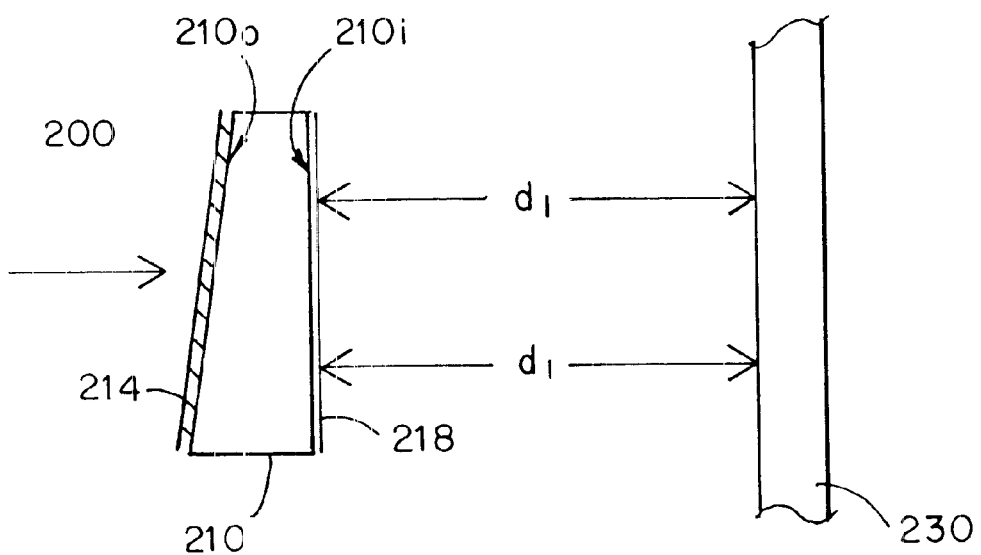
FIG. 2 is a simplified schematic of a Fabry-Perot cavity having only one partial mirror plate, the other mirror being the surface of interest.

Referring to FIG. 2, a simplified schematic of a Fabry-Perot cavity having only one partial mirror plate is shown ("optical resonator system 200" hereinafter). Note that the 2*xx* series items of FIG. 2 are essentially equivalent items to the 1*xx* series items of FIG. 1 unless otherwise described. Optical resonator system 200 includes a Fabry-Perot cavity formed by only one reference plate 210 having an inner partially reflective surface, rather than by two partly reflective plates. The above-mentioned plate is generally denoted as a "reference surface" or "reference plate". Reference plate 210 is generally constructed in a fashion similar to standard Fabry-Perot reference plates. However, unlike two partial mirror Fabry-Perot optical cavities, a second partly reflective plate does not exist explicitly. Instead, the second surface is a target surface, or surface of interest, upon which it is desired to enhance the resolution of a focused beam.

Referring again to FIG. 2, the optical resonator system 200 comprises at least one reference plate 210. As in a standard Fabry-Perot device, the reference plate 210 comprises at least one plate having a partly reflective inner surface. The inner surface 210*i* of the reference plate 210 may comprise a coating 218 that is either a dielectric coating or a metallic coating, in either single or multiple layers, as previously discussed, for the purposes of establishing the partial reflectance.

Partly reflective inner surface 210*i* is positioned substantially parallel to and at a distance d, from a surface of interest 230. A surface of interest 230 is any surface upon which it is desired to produce the beam narrowing for purposes of resolution enhancement. If optical system 200 is used for measurement of surface features of a reflective or partially reflective medium, then surface of interest 230 is the surface of which features are measured.

Figure 3:
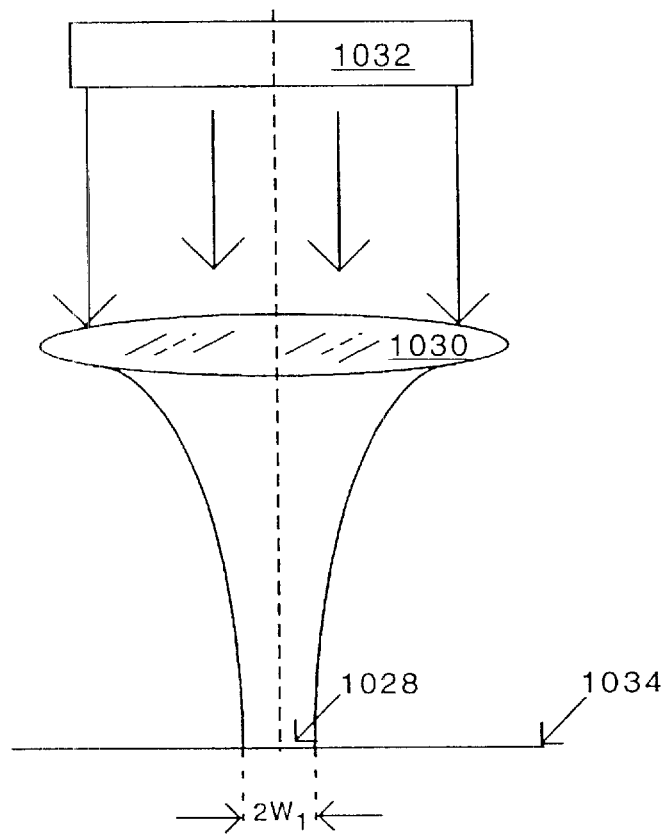
FIG. 3 shows a simplified prior art system depicting a focused light beam upon a surface of interest.
Figure 3:
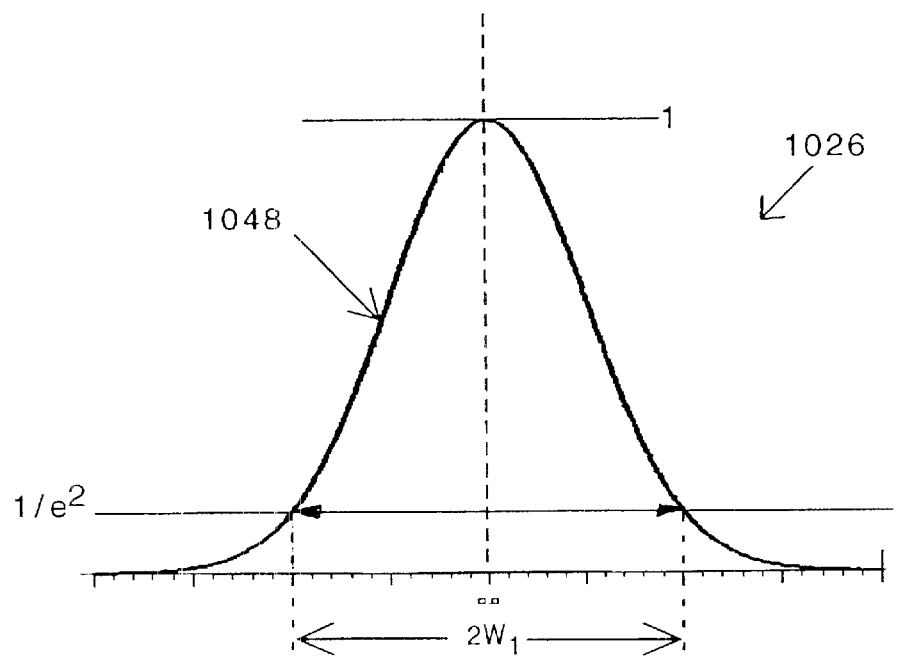

Referring to FIG. 3, a simplified prior art system for the focusing of a coherent beam is shown. The prior art system comprises an illumination system 1032 (shown here after beam collimation, which although not mandatory has been used herein for a simplified explanation,) and an optical system 1030. A light source (not shown herein) is imaged through the illumination system 1032 and the optical focusing system 1030 onto a surface of interest 1034. When illumination system 1032 is illuminated by a gaussian light source, the focused spot 1028 will possess an area having a radius equal to $W_1$ in the present example. The intensity profile 1048 of the focused spot on the surface of interest 1034 conforms to the graphical characteristic as shown in chart 1026 and as otherwise understood by those skilled in the art for a particular combination of light source, illumination system 1032 and focusing system 1034 according to the laws of gaussian beam concentration. These principles are also explained in the above-referenced text: *OPTICS*.

Figure 4:
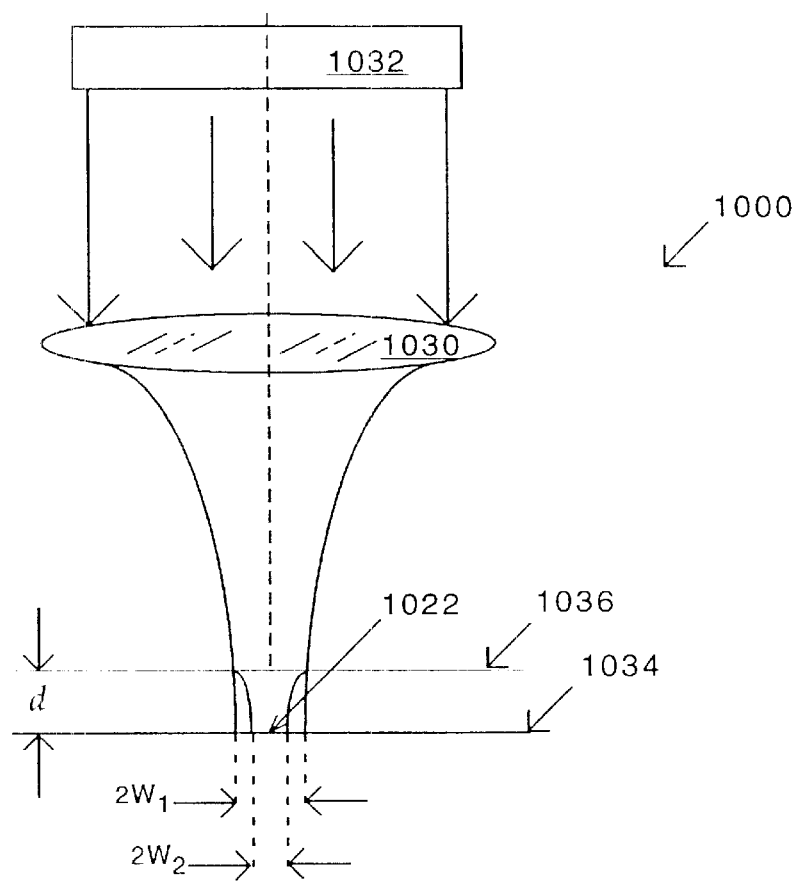
FIG. 4 shows a first embodiment of the present invention, a light beam narrowing system.
Figure 4:
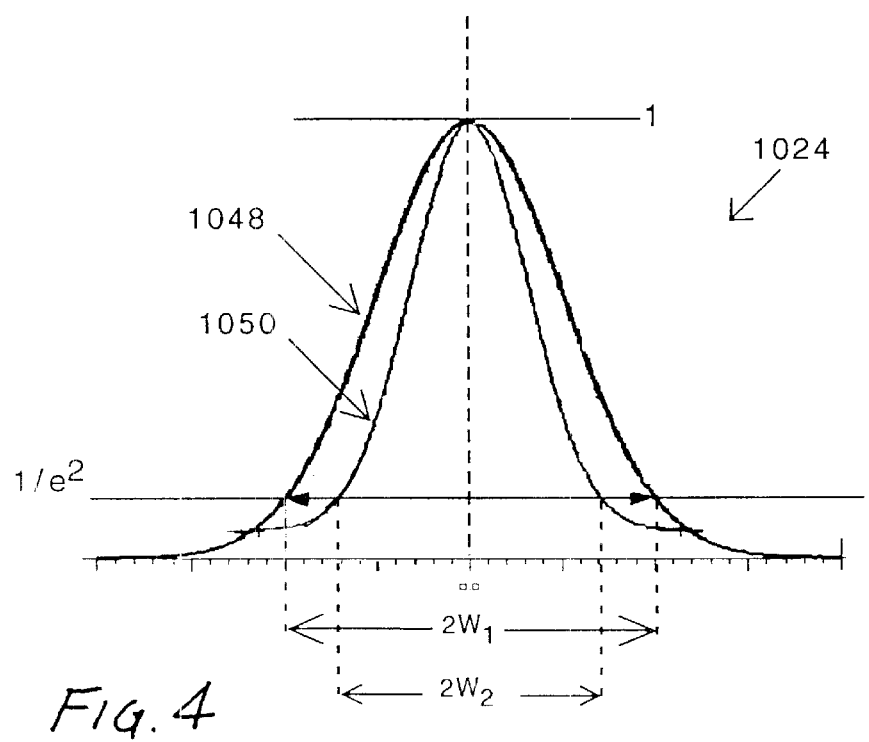

Referring now to FIG. 4, an embodiment of the present invention for narrowing a light beam is shown. Note that a similar item numbering protocol is used between FIG. 3 and FIG. 4 and unless otherwise specified, like numbered items are substantially identical. An embodiment of the present invention includes the placement of a reference surface parallel to a surface of interest and the adjustment of the distance between the two surfaces in a manner such that the size of a focused spot on the surface of interest is smaller than the smallest ideal spot size produced by system depicted in FIG. 3. A smaller size focused spot is produced by beam narrowing due to destructive multiple-beam interference within the Fabry-Perot optical cavity formed by a partly reflective surface 1036 and a surface of interest 1034. The spacing between partly reflective surface 1036 and surface of interest 1034 is adjusted so as to enhance the destructive effect at the edges of the gaussian contour, effectively narrowing the beam. At a point close to anti-resonance the first pass wave, the second pass wave, the third pass wave, etc. will interact with each other in constructive/destructive interference as is well known to those skilled in the art. The constructive/destructive interference will result in the cancellation of the "wings" or "tails" of the gaussian contour.

In the embodiment of the beam narrowing system depicted in FIG. 4, system 1000 comprises an illumination system 1032 (shown here after beam collimation, which although not mandatory has been used herein to simplify illustration), an optical system 1030, and a reference plate 1036 having a partly reflective inner surface. System 1000 further comprises a second mirror, or second plate, or surface of interest 1034 as in this case. Surface of interest 1034 has an approximate reflectivity as low as about 10%, and as high as 100%, and the inner reflective surface of the reference plate 1036, facing surface of interest 1034, has an approximate reflectivity of 50%, although this value may be as low as about 8%, and as high as about 98%. The light source (not shown herein) is imaged through the illumination system 1032 and the optical focusing system 1030 and is focused into the Fabry-Perot cavity through first mirror or reference plate 1036 onto surface of interest 1034. The cavity length d between the inner reflective surface of reference plate 1036 and surface of interest 1034 is tuned to obtain a minimum spot radius $W_2$ on the second plate. By way of example, reference is made to the prior art, shown in FIG. 3. Focused spot 1028 has a spot diameter 2 $W_1$ of 2 μm at the second plate. However, as shown herein in FIG. 4, in an example of an embodiment of the present invention, the placement of a reference plate 1036 between the illumination system 1032 and the second plate, or surface of interest 1034, and the tuning of the distance between the reference plate's 1036 partly reflective inner surface and the surface of interest 1034 reflective surfaces results in a light beam comprising a focused spot 1022 inside the Fabry-Perot cavity having a reduced spot diameter 2 $W_2$ of 1.58 μm at surface of interest 1034. The beam size depicted by intensity profile 1050 is substantially narrower than the beam size depicted by intensity profile 1048 in chart 1024. Intensity profile 1050 is the profile at surface of interest 1034 as understood by those skilled in the art.

While the embodiments of the invention described herein are described as being illuminated with a gaussian light source and the intensity profiles depicted by the figures conform to profiles produced by gaussian illumination, it will be understood by those skilled in the art that the present invention applies to light sources having other illumination profiles, for example sources having a uniform intensity profile. It should also be noted that the above example of a reduction in the spot diameter is an example and that other starting spot diameters may be reduced in a similar manner in other embodiments of the present invention.

Figure 5:
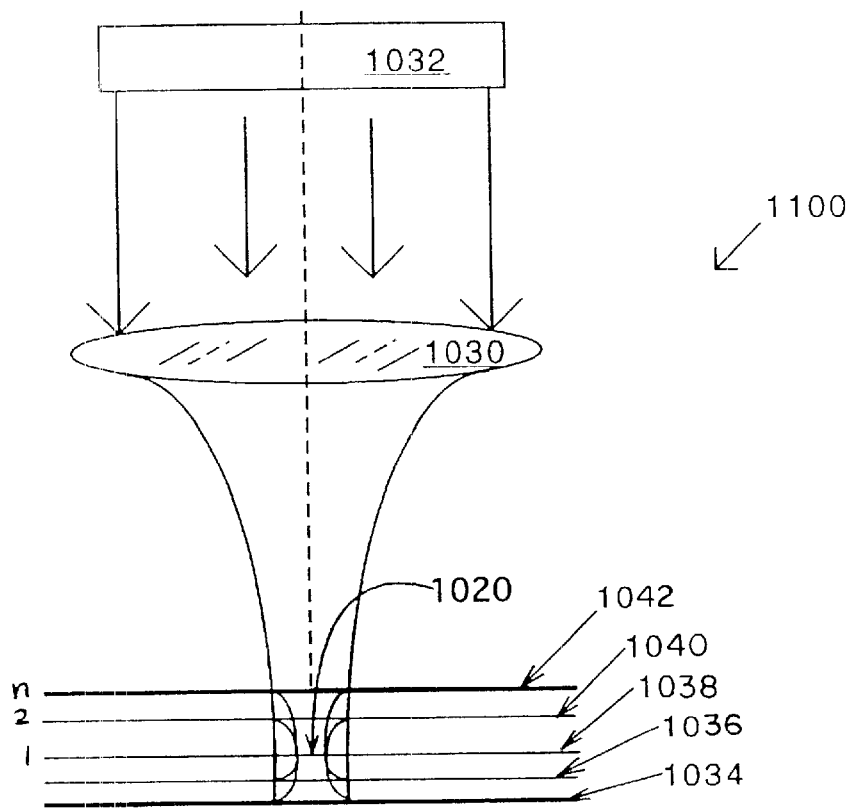
FIG. 5 shows a second embodiment of the present invention, a light beam narrowing system including a plurality of partially reflective surfaces.
Figure 5:
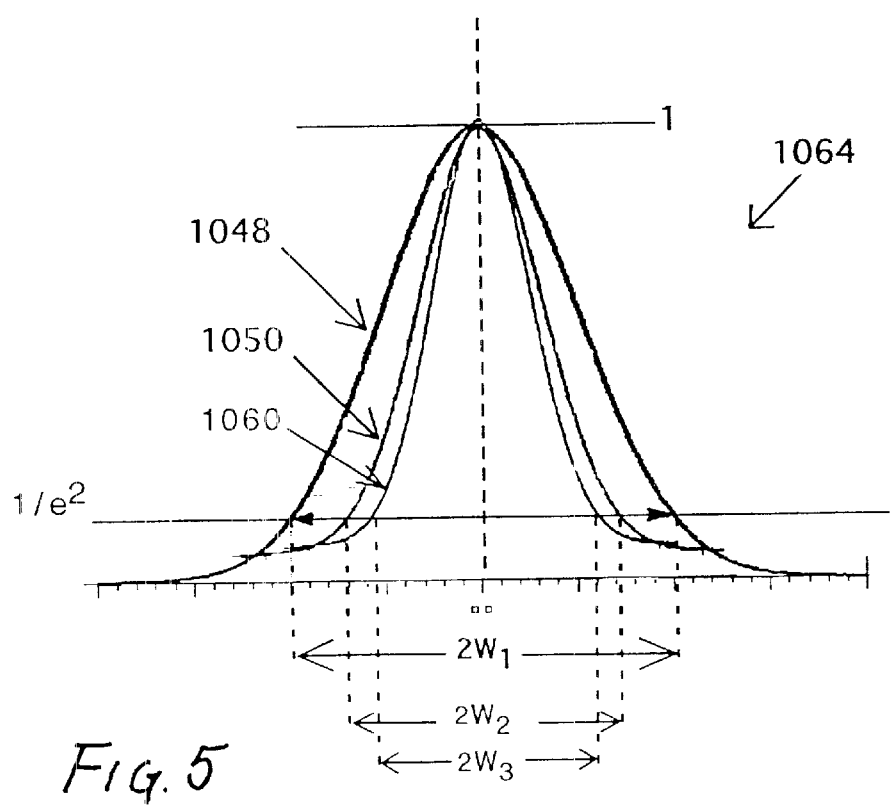

Referring to FIG. 5, a second embodiment of the present invention including a plurality of partially reflective surfaces is shown. Note that a similar item numbering protocol is used between FIG. 3, FIG. 4, and FIG. 5. Unless otherwise specified, like numbered items are substantially identical. A second embodiment of the present invention, as in the prior embodiment, includes a reference surface parallel to a surface of interest.

In the second embodiment, a series of interfaces forms a plurality of partly reflective surfaces above an underlying surface, each partly reflective surface having a unique specific reflectivity. As an example, this stack of partially reflective surfaces can be formed by interfaces between laminated films having differing indices of refraction, films having reflective coatings, optical coatings deposited on a media, film/adhesive layers, etc cetera.

The partly reflective surfaces and the underlying surface are adjusted spatially to assure a specific optical distance between each partly reflective surface, every other partly reflective surface and the underlying surface. Furthermore, each additional partly reflective surface forms an interface that represents a selectable target surface. The target surface is selected by adjusting the optical distances such that the minimum spot size is produced at a selected target surface. Since each partially reflective surface and the underlying surface can form a multiple Fabry-Perot device, the optical distances are all tuned simultaneously to produce the desired resonance between each of the surfaces. Each of the partially reflective surfaces or the underlying surface which may be fully reflective can be selected as a surface of interest. By adjusting the optical distances appropriately, any of the above-mentioned surfaces can be selected as a target surface by tuning the optical distances such that the beam narrowing effect is produced at the selected surface.

In this alternative embodiment of the beam narrowing system, a system 1100 comprises an illumination system 1032 (shown here after beam collimation, which although not mandatory has been used herein for a simplified explanation), an optical focusing system 1030, and a series of partially reflective surfaces 1036, 1038, 1040 and 1042. The underlying surface 1034 can be totally reflective.

In this second embodiment of the present invention, the underlying surface 1034 is covered by optical layers forming partially reflective surfaces 1036, 1038, 1040, and 1042, each separated by a specific optical distance from each other, above underlying surface 1034. The partly reflective surfaces 1036, 1038, 1040, and 1042 will form multiple Fabry-Perot cavities as is known by those skilled in the art. Thus, the total reflectivity from a surface of interest is contributed to by a plurality of partly reflective surfaces 1036, 1038, 1040, and 1042, and underlying surface 1034. Each of the above-mentioned surfaces is adjusted spatially to assure a specific distance between each surface. These relationships may be thought of as forming a matrix of surfaces and properties.

The partly reflective surfaces 1038, 1040, and 1042 represent additional partly reflective surfaces 1, 2, and n with respect to the first embodiment which had only two reflective surfaces. It should be noted that although three additional partly reflective surfaces, 2 plus an $n^{th}$ partly reflective surfaces, are shown herein, as few as one additional partly reflective surface, e.g. partly reflective surface 1040 (partly reflective surface 2) in addition to the partly or fully reflective underlying surface 1034 may be used or any number of additional partly reflective surfaces greater than the number shown may also be used. Although the reflectivity of the underlying surface 1034 may be as high as 100%, those skilled in the art will recognize that the selection of the percent reflectivity of partly reflective surfaces 1036, 1038, 1040, and 1042 will vary as determined by the effects desired from the multiple Fabry-Perots formed thereby.

As described above, a light source (not shown herein) is imaged through illumination system 1032 and optical focusing system 1030 and is focused into a Multiple Fabry-Perot cavity formed by partially reflective surfaces 1042, 1040, 1038 and 1036 and the underlying surface 1034. The light source may be imaged selectively upon any of the surfaces of the multiple Fabry-Perot device, and the beam narrowing phenomena will cause a reduced beam spot size at any selected target surface from among any of the surfaces. Also, the additional resonances produced between the surfaces will act in a fashion that is analogous to that of multiple coatings upon optical lenses, resulting in a further reduction in the reduced beam spot size over the reduced beam spot size of the first embodiment. This enhanced reduced beam spot size will occur at the selected target surface.

By way of example, reference is made to the prior art, shown in FIG. 3. The focused light beam 1042 has a spot diameter 2 $W_1$ of 2 μm at the second plate. However, as shown in FIG. 4, in an example of an embodiment of the present invention, the placement of a reference plate 1036 between the illumination system 1032 and the second plate, or surface of interest 1034, and the tuning of the distance between the reference plate's 1036 partly reflective inner surface and the surface of interest 1034 results in a light beam focused inside the Fabry-Perot cavity having a focused spot 1022 diameter 2 $W_2$ of 1.58 μm at the surface of interest's 1034 reflective surface. Additionally, as shown in FIG. 5, on Chart 1064, in an alternate embodiment of the present invention, the presence of additional partly reflective surfaces 1038, 1040, and 1042 when tuned to form multiple Fabry-Perot cavities will cause a reduced beam size intensity profile 1060 that is narrower than the intensity profile 1050 of the embodiment of the present invention depicted in FIG. 5. It should be noted that chart 1064 shows only the intensity profiles for the selected target surface. Other partly reflective surfaces will have their own beam intensity profile.

Referring again to chart 1064, the reduced beam size intensity profile 1060 yields a focused spot 1020 of diameter 2 $W_3$ at the selected target surface. It should be noted that all of the cavities formed between surfaces 1034, 1036, 1038, 1040 and 1042 will contribute to the beam narrowing at the selected target surface. The enhanced beam narrowing function of the second embodiment of the present invention is cumulative in proportion to the number n of additional partly reflective surfaces. Due to the resonance properties of the multiple Fabry-Perot cavities, the beam narrowing cumulative effect is not directly additive nor multiplicative based upon the number of additional partly reflective surfaces.

Again, as explained previously, the further reduced beam size of intensity profile 1060 conforms to chart 1064 and as understood by those skilled in the art. When system 1100 is illuminated by a gaussian source, the focused spot 1020 will have a profile in accordance with the laws of gaussian concentration. Beam narrowing makes it possible to resolve features of the selected target surface in greater detail. Thus, the enhanced beam narrowing phenomena also allows the resolution of features at any selected target surface from among any of the partly reflective surfaces 1036–1042 or the underlying surface 1034, and the detectable features will be even smaller than those resolvable by the 40% reduction beam narrowing phenomena of the prior embodiment of the present invention.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. A system of beam narrowing for resolution enhancement, comprising, in combination:
    an illumination system;
    a first reflective surface positioned in a plane relative to said illumination system;
    a second reflective surface positioned in a plane relative to said illumination system and disposed between an optical focusing system and said first reflective surface;
    said optical focusing system positioned in a plane relative to said illumination system, said optical focusing system cooperating with said illumination system, to image a light source through said illumination system, through said optical focusing system and onto said first reflective surface and said second reflective surface;
    wherein said first reflective surface is substantially parallel to said second reflective surface, wherein said first reflective surface is further positioned at a tuned optical distance from said second reflective surface, and wherein said tuned optical distance is defined as that value wherein said light source imaged onto one of said first reflective surface and said second reflective surface selected as a target surface forms a minimum radius spot size upon said selected target surface.

2. The system of claim 1 wherein said selected target surface is selected as said first reflective surface.

3. The system of claim 1 wherein said selected target surface has a reflectivity of interest between about 10% and about 100%.

4. The system of claim 1 wherein said first reflective surface has a reflectivity in the range from about 7% to about 98%.

5. The system of claim 4 wherein said first reflective surface has a reflectivity from about 50% to about 98%.

6. The system of claim 1 wherein said first reflective surface and said second reflective surface are boundaries of an optical layer produced by an optical coating, said layer having an optical thickness corresponding to said tuned optical distance.

7. The system of claim 1 wherein said first reflective surface is selected as said target surface, and wherein said light source imaged onto said first reflective surface forms a minimum radius spot size upon said first reflective surface.

8. The system of claim 1, further comprising at least one additional partly reflective surface positioned in a plane relative to said illumination system and disposed between said first reflective surface and said second reflective surface, and wherein said at least one additional partly reflective surface is selectable as said selected target surface by adjusting said first optical distance in conjunction with at least one other optical distance between said first reflective surface and said at least one additional partly reflective surface and wherein said at least one other tuned optical distance is defined as that value wherein said light source imaged onto said selected target surface forms a minimum radius spot size upon said selected target surface.

9. The system of claim 8, wherein said at least one additional partly reflective surface is selected as said target surface.

10. The system of claim 9, wherein said selected target surface is a member of the class comprised of partly reflective surfaces.

11. The system of claim 9, wherein said at least one additional partly reflective surface has a reflectivity from about 10% to about 98%.

12. The system of claim 11, wherein said first reflective surface has a reflectivity in the range from about 7% to about 98%.

13. The system of claim 11, wherein said first reflective surface has a reflectivity from about 50% to about 98%.

14. The system of claim 8 wherein said at least one additional partly reflective surface is a boundary of an optical layer produced by an optical coating, said layer having a thickness corresponding to a difference between said at least one other tuned optical distance corresponding to said at least one additional partly reflective surface forming said boundary and another tuned optical distance corresponding to an opposite boundary formed by the opposite side of said optical layer.

15. A system of beam narrowing for resolution enhancement, comprising, in combination:
    an illumination system;
    a first reflective surface positioned in a plane relative to said illumination system;
    a second reflective surface positioned in a plane relative to said illumination system and disposed between an optical focusing system and said first reflective surface;
    said optical focusing system positioned in a plane relative to said illumination system, said optical focusing system cooperating with said illumination system, to image a light source through said illumination system, through said optical focusing system and onto said first reflective surface and said second reflective surface; and
    at least one additional partly reflective surface positioned in a plane relative to said illumination system and disposed between said first reflective surface and said second reflective surface, and wherein one of said first reflective surface, said second reflective surface and said at least one additional partly reflective surface is selectable as a target surface by adjusting a first optical distance in conjunction with at least one other optical distance between said first reflective surface and said at least one additional partly reflective surface and wherein said at least one other tuned optical distance is defined as that value wherein said light source imaged onto said selected target surface forms a minimum radius spot size upon said selected target surface.

16. The system of claim 15, wherein said second reflective surface has a reflectivity between about 10% and about 100%.

17. The system of claim 15, wherein said first reflective surface has a reflectivity in the range from about 7% to about 98%.

18. The system of claim 17, wherein said first reflective surface has a reflectivity from about 50% to about 98%.

19. The system of claim 15, wherein said at least one additional partly reflective surface has a reflectivity from about 10% to about 98%.

20. The system of claim 19, wherein said first reflective surface has a reflectivity in the range from about 7% to about 98%.

21. The system of claim 20, wherein said first reflective surface has a reflectivity from about 50% to about 98%.

22. The system of claim 15, wherein said at least one additional partly reflective surface is a boundary of an optical layer produced by an optical coating, said layer having a thickness corresponding to a difference between said at least one other tuned optical distance corresponding to said at least one additional partly reflective surface forming said boundary and another tuned optical distance corresponding to an opposite boundary formed by the opposite side of said optical layer.

23. The system of claim 22, wherein said first reflective surface and said at least one additional partly reflective surface are boundaries of optical, layers produced by optical coatings, wherein each of said layers has a corresponding thickness such that said at least one additional tuned optical distance is determined by said corresponding thickness.

24. A method of beam narrowing for resolution enhancement, comprising:

imaging a light source from an illumination system, through an optical focusing system and onto a first reflective surface and a second reflective surface;

positioning said first reflective surface between said optical focusing system and said second reflective surface such that a Fabry-Perot cavity is formed between said first reflective surface and said second reflective surface; and adjusting an optical distance between said first reflective surface and said second reflective surface such that a minimum radius spot size from said imaged light source is produced at a selected target surface selected from one of said first reflective surface and said second reflective surface.

25. The method of claim 24, further comprising:

positioning at least one additional partly reflective surface between said first reflective surface and said second reflective surface such that multiple Fabry-Perot cavities are formed between said first reflective surface, said second reflective surface and said at least one additional partly reflective surface; and further adjusting at least one additional optical distance between said first reflective surface and said at least one additional partly reflective surface such that a minimum radius spot size from said imaged light source is produced at said selected target surface selected from one of said first reflective surface, said second reflective surface and said at least one additional partly reflective surface.

* * * * *